United States Patent [19]

Matsunaga et al.

[11] Patent Number: 5,258,324
[45] Date of Patent: Nov. 2, 1993

[54] MEGAKARYOCYTE COLONY STIMULATING FACTOR AND PROCESS FOR ITS PREPARATION

[75] Inventors: Keita Matsunaga, Yokohama; Shinichiro Kuriya, Tokyo; Kiyoyuki Ogata, Tokyo; Hiroyuki Hamaguchi, Tokyo; Chuhei Nojiri; Osamu Makabe, both of Yokohama; Takeo Nomura, Tokyo; Kozo Nagaoka, Yokohama, all of Japan

[73] Assignee: Meiji Seika Kaisha, Ltd., Japan

[21] Appl. No.: 668,493

[22] PCT Filed: Sep. 21, 1989

[86] PCT No.: PCT/JP89/00960

§ 371 Date: Mar. 20, 1991

§ 102(e) Date: Mar. 20, 1991

[87] PCT Pub. No.: WO90/03397

PCT Pub. Date: Apr. 5, 1990

[30] Foreign Application Priority Data

Sep. 21, 1988 [JP] Japan ................... 63-234722

[51] Int. Cl.$^5$ .............. C12P 21/02; A01N 37/18; A61K 37/00; C07K 3/00
[52] U.S. Cl. ................... 435/70.1; 514/2; 514/21; 530/350; 530/351; 530/399
[58] Field of Search .......... 435/70.1; 514/2, 21; 530/350, 351, 399

[56] References Cited

U.S. PATENT DOCUMENTS 4,965,195 10/1990 Naren et al. ............... 435/69.52

OTHER PUBLICATIONS

Burgess et al., *Biochem J.* 185, 1980, pp. 301-314.
R. Hoffman et al., Journal of Clinical Investigation, vol. 75, No. 4, "Purification and Partical Characterization of a Megakaryocyte Colony-Stimulating Factor from Human Plasma," pp. 1174–1182 (1985).
D. Geissler et al., Journal of Immunology, vol. 137, No. 8, "The Influence of T-Lymphocyte Subsets and Humoral Factors on Colony Formation by Human Bone Marrow and Blood Megakaryocyte Progenitor Cells In-Vitro," pp. 2508–2513 (1986).

*Primary Examiner*—Douglas W. Robinson
*Assistant Examiner*—L. Blaine Lankford
*Attorney, Agent, or Firm*—Larson and Taylor

[57] ABSTRACT

A novel megakaryocyte colony stimulating factor has been isolated from the supernatant of the culture obtained by cultivating a cell strain of a human large cell lung cancer. When the factor is applied to human or murine bone-marrow cells in vitro, it forms a megakaryocyte colony. Also, the factor increases the number of platelets in peripheral blood in vivo.

4 Claims, 3 Drawing Sheets

MEGAKARYOCYTE COLONY STIMULATING FACTOR AND PROCESS FOR ITS PREPARATION

TECHNICAL FIELD

This invention relates to a novel megakaryocyte colony stimulating factor comprising or composed of such a protein which has been isolated from the supernatant of the culture as obtained by cultivation or culturing of a cell strain of a human large cell lung cancer, and which exhibits an activity of forming a megakaryocyte colony from human or murine bone marrow cells when the factor is applied to the bone marrow cells in vitro, and also exhibits an activity of proliferating megakaryocytes in spleen and an activity of increasing the number of platelets in peripheral blood in vivo. This invention also relates to its preparation process.

BACKGROUND ART

Platelets play important roles for promotion of thrombus formation and blood coagulation which both take place in such course of hemostasis that the bleeding as caused by a vascular puncture can stop naturally. In human beings, these platelets are released into the blood stream from the megakaryocytes which are present in the bone marrow and which have been differentiated from myeloid stem cells via the megakaryocyte progenitor cells.

Megakaryocyte colony stimulating factor (abbreviated as "Meg-CSF") is present in the blood of healthy human beings or mammals, and is a physiologically active substance which is said to act on the myeloid stem cells and/or megakaryocyte progenitor cells to promote the differentiation of these cells into megakaryocytes and proliferation of such megakaryocytes. The activities of Meg-CSF are measured in terms of the activity of forming the megakaryocyte colony from human or murine bone marrow cells in vitro. At present, it is recognized that the activities of the megakaryocyte colony stimulating factor are found in the urine from patients with aplastic anemia [Kawakita, M. et al., "Blood", 61, 556 (1983)], the plasma from patients with amegakaryocytic thrombocytopenic purpurea [Hoffman, R. et al., "J. Clin. Invest.", 75, 1174 (1985)] and the supernatant recovered from the culture of human peripheral lymophocytes stimulated by phytohemagglutinin (PHA) [Messner, H. A., et al., "J. Cell Physiol. Suppl.", 1, 45]. When intentions are made to recover and purify the megakaryocyte colony stimulating factor and then to formulate it into medicinal drugs, it is however difficult to obtain the urine and plasma etc. of such patients in the form of a uniform raw material in a large quantity as the starting material to be used for the preparation of Meg-CSF, because they are all biological materials, exhibit individual changes and carry the potential danger of infection by virus or bacteria.

On the other hand, there have been reported a megakaryocyte stimulatory factor (MSF) which has been isolated from the supernatants of the cultures of human embryonic kidney cells or from thrombocytopenic patient's plasma and which has a molecular weight of 15,000 daltons on SDS-PAGE, an isoelectric point of 5.1 and the activity of promoting the protein-synthesis in the megakaryocyte cells, and also process for preparation of MSF (see European Patent Publication No. 0 260 918 A2 or Japanese Patent Application first publication "Kokai" No. 239298/88). This known MSF can specifically act on megakaryocytes but cannot show the activities of Meg-CSF.

An object of the present invention is to find out a stable material source available for the preparation of the megakaryocyte colony stimulating factor (Meg-CSF) and also to produce the megakaryocyte colony stimulating factor from that material source. Another object of the present invention is to purify the thus-obtained Meg-CSF substance to a purity such that it can be used as a medicinal drug.

We, the present inventors, have thus investigated into a variety of animal cell strains which were available in a large quantity as the uniform starting materials. As a result, the activities of the megakaryocyte colony stimulating factor (Meg-CSF) have now been discovered to be developed in the supernatants of the culture (hereinafter called simply "the supernatant") which are obtained by culturing a human large cell lung cancer cell strain PC-13 (commercially available from Immunobiological Laboratories, Co., Ltd., located at Fijioka City, Gumma-ken, Japan). With a view toward conducting efficient isolation and purification of the Meg-CSF substance, we, the present inventors, have further selected a strain having a high Meg-CSF-productivity and devised a cell culturing method with making use of a serum-free medium. We have now succeeded in separating, isolating and purifying the Meg-CSF substance from the supernatant of the culture which has been obtained by cultivation or culturing of cells of the strain PC-13 in accordance with the serum-free culturing method with the serum-free culture medium, while using the potencies of the megakaryocyte colony stimulating factor as an index. We, the present inventors, have also found that a purified product of Meg-CSF so obtained exhibits the activity of promoting proliferation of megakaryocyte progenitor cells and megakaryocytes when the purified Meg-CSF product is applied to them in vivo and also exhibits the activity of increasing the number of platelets in peripheral blood when the purified Meg-CSF product is administered to mammal. By the measurements of physicochemical properties and biological properties of the purified Meg-CSF product thus obtained, it has also been confirmed that this Meg-CSF product is a novel substance. The present invention has been completed on the basis of these findings.

DISCLOSURE OF THE INVENTION

In a first aspect of the present invention, there is thus provided a megakaryocyte colony stimulating factor which comprises a protein as isolated from the supernatant of the culture obtained by cultivation of a cell strain of a human large cell lung cancer and which exhibits the activity of forming a megakaryocyte colony when said factor is applied to human or murine bone marrow cells in vitro, and also exhibits the activity of increasing the number of platelets in peripheral blood in vivo.

In a second aspect of the present invention, there is also provided a megakaryocyte colony stimulating factor which comprises a protein as isolated from the supernatant of the culture obtained by cultivation of a cell strain of a human large cell lung cancer and which exhibits the activity of forming a megakaryocyte colony when said factor is applied to human or murine bone marrow cells in vitro, and also exhibits the activity of increasing the number of platelets in peripheral blood in vivo and further has the following properties:

(a) Said factor can be isolated from the supernatant of the culture of human large cell lung cancer cell strain PC-13 or from the supernatant of the culture of human lung cancer cell strain MC-1 (deposited under the deposit number "FERM BP-2574" with "Fermentation Research Institute", Agency of Industrial Science and Technology, Ministry of International Trade and Industry, Government of Japan, in terms of the Budapest Treaty) having been isolated as a monoclonal strain from the PC-13 strain;

(b) Molecular weight: 24,000 (as measured by gel-filtration);

(c) Isoelectric point: 4.5–5.5 (as measured by isolectric chromatography);

(d) Thermal stability of activities: the factor can be deactivated when the factor is heated at 80° C. for 30 minutes, and hence the activities of the factor do not have thermal stability;

(e) Stability of activities against enzyme: The activities of the factor remain stable even when the factor is treated with neuraminidase;

(f) Presence or absence of activities of cytokines and the like: The factor does not show the activities of any one of interleukin-2 (IL-2), interleukin-6 (IL-6), tumor necrosis factor (TNF) and erythropoietin (EPO);

(g) Antigenecity: The activities of the factor are not neutralized by any one of anti-interleukin-1α antibody, anti-interleukin-1β antibody, anti-human GM-CSF antibody and anti-human interleukin-3 antibody. When evaluated by radioimmunoassay, the factor does not exhibit immunological cross reaction with any one of prolactin, thyroid-stimulating hormone (TSH), growth hormone (GH), insulin, vasopressin (ADH) and adrenocorticotropic hormone (ACTH);

(h) Stability of activities against solubilizers: When the factor is treated with sodium dodecylsulfate (SDS) or guanidine hydrochloride, the activities of the factor are partially lost so that the activities of the factor are unstable in this point. However, the activities of the factor remain substantially stable even when the factor is treated with a non-ionic surface-active detergent; such as "Tween 20" [i.e., polyoxyethylene(20) sorbitol monolaurate], "Nonidet P40" [i.e., polyoxyethylene(9)-p-tert-octylphenol] and "Triton X-100" [(i.e., polyoxyethylene(9-10)-p-tert-octylphenol];

(i) Characteristic physiological activities: The factor shows the activity of forming a megakaryocyte colony when the factor is applied to human or murine bone marrow cells in vitro. The factor also exhibits the activity of promoting proliferation of megakaryocytes and megakaryocyte progenitor cells in the spleen and the activity of increasing the number of platelets in peripheral blood when the factor is administered to a mouse.

The megakaryocyte colony stimulating factor according to the second aspect of the present invention has a molecular weight of 24,000 (as measured by gel-filtration and an isoelectric point of 4.5–5.5 and is hence recognized to constitute a single protein substance.

In a third aspect of the present invention, there is also provided a process for the preparation of a megakaryocyte colony stimulating factor, which comprises cultivating a cell strain of a human large cell lung cancer; separating the supernatant containing the megakaryocyte colony stimulating factor, from the resulting culture of the cell strain, recovering the megakaryocyte colony stimulating factor from the supernatant obtained, and then purifying said factor.

In this process of the present invention, it is feasible to use, as the cell strain of the large cell lung cancer to be cultured, a cell strain PC-13 thereof (which is available freely upon request from "Immunobiological Laboratories Co., Ltd.", located at Fujioka City, Gumma-ken, Japan). It is also feasible to use a human lung cancer strain MC-1 which has been isolated as a monoclonal strain by the present inventors from the above-mentioned cell strain PC-13. Human lung cancer strain MC-1 has been deposited since Aug. 31, 1989 under the deposit number of "FERM BP-2574" in terms of the Budapest Treaty in a depository "Fermentation Research Institute", Agency of Industrial Science and Technology, Ministry of International Trade and Industry, Government of Japan, located at Tsukuba City, Ibaraki-ken, Japan.

In the process of the present invention, it is preferable to culture the human large cell lung cancer cell strain in a serum-free medium.

We, the present inventors, have proceeded with further investigations in order to find out such a composition of the culture medium that is most suitable for culturing a cell strain of the human large cell lung cancer, especially of the cell strain PC-13 and the cell strain MC-1 described above. As a result, a new serum-free medium has now been prepared by adding several auxiliary components to RPMI-1640 medium which is known as a culture medium for culturing the animal cells. This new serum-free medium has now been named "RPMI-HPTS medium". This RPMI-HPTS medium contains, per 10 l of the medium, 104 g (as measured in a powder form) of RPMI-1640 medium, 12 g of sodium hydrogen carbonate, 400 mg of penicillin G, 400 mg of streptomycin, 50 mg of transferrin, 200 μg of selenious acid, 1.0 mM of sodium pyruvate, 15.0 mM of N-2-hydroxyethylpiperazin-N'-2-ethanesulfonic acid (this compound is a buffering agent which is normally abbreviated as "HEPES" and its chemical formula is $C_8H_{18}N_2O_4S$) and the balance of sterilized water, and does not contain any serum component.

We have found that the RPMI-HPTS medium is well suitable for producing the megakaryocyte colony stimulating factor of this invention by culturing the aforesaid cell strain PC-13 or the human lung cancer cell strain MC-1 described above.

In a still further aspect of the present invention, therefore, there is also provided a process for the preparation of a megakaryocyte colony stimulating factor, which comprises culturing the human lung cancer cell strain MC-1 (as deposited under the deposit number of FERM BP-2574) in the RPMI-HPTS midium having the above-described composition at a temperature of 35°–38° C. under air which ocntains 5% $CO_2$ and is saturated with humidity; and continuing the culturing of the cells until the megakaryocyte colony stimulating factor is produced and accumulated in the supernatant of the resulting culture of the cells.

BEST MODE FOR WORKING THE INVENTION

In order to obtain the megakaryocyte colony stimulating factor (Meg-CSF) of this invention, generally, a cell strain of the human large cell lung cancer, especially the above-described cell strain PC-13 or human lung cancer cell strain MC-1 is cultured in a culture medium which is employed generally for the cultivation of animal cells, whereby the Meg-CSF substance is produced and accumulated in the supernatant of the resulting culture of the cells, namely the conditioned medium. As the culture medium usable for this process, for example, RPMI-1640 medium, Dulbecco's Modified Eagle's Medium, Ham's F12 medium and the like, which are all known, can be used, either singly or in combination of two or more of them. The culture medium may be added with 0-10% of any of fetal calf serum or selenious acid, pyruvic acid, ethanolamine, transferrin, serum albumin and HEPES, and/or the like. Desirably, the culturing can be conducted by inoculating the cells, which are to be cultured, to a culture medium, for example, at an inoculum size of $1\times 10^4$-$1\times 10^6$ cells/ml, and incubating the medium at a temperature of 35°-38° C. at which growth and proliferation of the cells are feasible, preferably at 37° C. in humidity-saturated air in the presence of 5% $CO_2$. Usable exemplary culture vessels include various flasks, Petri dishes, roller bottles and the like, which are generally employed for the culturing of animal cells. It is also possible to culture the cells in a spinner bottle by using a microcarrier. When the culturing is conducted under the serum-free conditions or under conditions of a low-serum-concentration (2% or less), it is desirable to preliminarily treat a cell-adhering surface of the inner wall of each culture vessel with collagen, gelatin or the like. A culturing time of 2-6 days or so is generally sufficient. Thereafter, the supernatant (the conditioned medium) is separated from the culture so obtained. This supernatant contains the Meg-CSF substance as produced of the present invention.

Cells of the strain PC-13 are adherent cells, which are of the type that they cannot grow and proliferate unless they are allowed to have adhered on a solid surface upon culturing of the cells. A method which is generally employed for the cloning of adherent cells may be used in order to isolate, from this PC-13 strain, such a monoclonal strain having a high Meg-CSF-producing ability. For example, the limiting dilution technique, a colony-forming technique or the like can be used for that purpose. It is then desirable that the cells, which have been obtained by any one of these techniques, are each allowed to individually and separately grow and proliferate to a cell concentration of $1\times 10^5$-$1\times 10^6$ cells/ml in a medium, investigating the potencies of the megakaryocyte colony stimulating factor in the supernatants of their resulting individual cultures with aid of an "in vitro" evaluation system, thereby detecting a cloned cell strain having a high ability to produce the Meg-CSF substance of this invention, and then allowing the detected cloned cell strain of the high Meg-CSF productivity singly to grow and proliferate further.

The recovery of the Meg-CSF substance of this invention from the supernatant containing it therein, and its purification can be achieved by effecting dialysis, Ultra-filtration, salting out, gel-filtration, ion-exchange chromatography, isoelectric chromatography, hydroxyapatite chromatography, hydrophobic chromatography, lectin column chromatogrphy, reversed phase chromatography, and the like, in a proper combination of two or more of them. Described more specifically, it is convenient to conduct the recovery and purification of the Meg-CSF substance, for example, by the following 5-step process:

1. Chromatography on hydroxyapatite column

The supernatant containing Meg-CSF is caused to pass through a column of hydroxyapatite (HA) so that the active substance is adsorbed on the HA column. The active substance so adsorbed is then separated from the column by elution. Desirably, this elution may be effected with an aqueous solution of sodium phosphate or calcium phosphate, whose pH and concentration are approximately 7-8 and 0.2-0.5M, respectively. The elution may be conducted while monitoring the absorbance of eluate fractions for ultraviolet rays (UV) of 280 nm wavelength which proteins absorb. Eluate fractions showing a UV absorption at this wavelength value are combined together and collected as an active fraction.

2. Chromatography on Con A-conjugated carrier column

The active fraction as eluted and collected above is caused to pass, as it is, through a column of Con A (namely, Concanavalin A)-conjugated carrier, for example, a Con A-conjugated agarose column, and such fractions having passed without being adsorbed in this column are collected. Among the fractions so collected, active factions showing the UV absorption at 280 nm are combined together in a similar manner to the above-described procedure by monitoring the UV absorbance at 280 nm. The active fractions thus combined are called the "Con A-nonbound fraction".

3. Ion-exchange chromatography

The salt concentration of the above Con A-nonbound fraction is then lowered using a method such as dialysis or Ultra-filtration. Next, the fraction is caused to pass through a colum of an ion-exchanger to have the active substance adsorbed. The active substance is recovered into active fractions by desorption while eluting the adsorbed active substance from the ion-exchanger. Illustrative examples of the ion-exchanger include anion-exchangers, specifically "DEAE-TOYOPEARL" (product of TOSOH CORP.), "DEAE-Sepharose" (product of Pharmacia LKB Biotechnology), "Q-Sepharose" (product of Pharmacia LKB Biotechnology), and "Mono-Q" (product of Pharmacia LKB biotechnology). Desirably, the adsorption of the active substance on the ion-exchanger may be carried out at pH 7-9 and at a salt concentration of about 0.01-0.5M, and the elution may be carried out by salt gradient elution method in the range of about 0.1-1M. and at pH 7-9.

4. Gel filtration

The active fraction obtained from the ion-exchange chromatography in the preceding step is then caused to pass through a column of a gel-filtration carrier, either as such, or after the active fraction has been concentrated by Ultra-filtration, lyophilization or the like. And, the active fraction is developed in the column. The active fraction is then recovered from the column by elution. Usable examples of the gel-filtration carrier include those capable of fractionating molecular weights in the range of from 10,000 to 500,000 or so, specifically "Ultrogel" (product of LKB), "Sephadex" (product of Pharmacia LKB Biotechnology), "Sephacryl" (product of Pharmacia LKB Biotechnology), "TOYOPEARL" (product of TOSOH CORP.), "Bio-Gel" (product of Bio-Rad Laboratories), and "TSK gel G2000 SW" (product of TOSOH CORP.). In the gel-filtration chromatography, the equilibration and development may desirably be effected at pH 7-8 and a salt concentration of about 0.05-0.3M.

5. Hydroxyapatite chromatgraphy

The active fraction obtained from the preceding gel-filtration step is then adsorbed in a column of hydroxyapatite (HA), followed by elution for recovery of the fraction so adsorbed. Desirably, the adsorption can be conducted with aid of an aqueous sodium phosphate or calcium phosphate solution of pH 7-9 and a concentration of about 0.01-0.05M, and the elution can be performed at pH 7-9 by the salt gradient elution technique with sodium phosphate or calcium phosphate at concentrations of 0.01–0.5M or so.

Detection of the Meg-CSF substance of this invention in each of the above steps can be effected by using, as a marker, at least one of the in vitro activities of the megakaryocyte colony stimulating factor.

By the way, the process for recovery and purification of the Meg-CSF substance comprising the above-mentioned five steps is merely given to illustrate the recovery of the new substance of this invention. Of course, the recovery and purification of Meg-CSF may be achieved by means of any other procedures.

The megakaryocyte colony stimulating factor (Meg-CSF) substance according to the present invention promotes the processes of "in vitro" formation of the megakaryocyte colony from human or murine bone marrow cells and also accelerates "in vivo" proliferation of megakaryocyte progenitor cells and megakaryocytes and also "in vivo" increase of platelets. The megakaryocyte colony stimulating factor substance are useful as a reagent for studying the differentiation from megakaryocyte progenitor cells to megakaryocyte cells and the proliferation of megakaryocytic cells, and also be useful as medicinal products. The megakaryocyte colony stimulating factor according to the present invention can be effectively employed for therapeutic treatment of certain thrombocytopenia, namely, thrombocytopenia after administration of anti-cancer drugs, thrombocytopenia involved subsequently to radiotheraphy, thrombocytopenia due to megakaryocyte colony stimulating factor deficiency, thrombocytopenia due to aplastic anemia, and thrombocytopenia occurring after bone marrow transplantation. Further, Meg-CSF of this invention can also be useful for therapeutic treatment of leukemia by promoting the differentiation of megakaryoblastic leukemia cells to megakaryocytes. In addition, Meg-CSF of this invention can also be employed as a substitute or auxiliary agent for platelets upon transfusion of the latter. The Meg-CSF substance of this invention may be administered intraperitoneally, intravenously or subcutaneously. Meg-CSF of this invention may be mixed with various conventional excipients to formulate medicinal compositions of various forms which can be administered.

As described above, we, the present inventors, have also succeeded in isolating a human lung cancer cell strain MC-1, as a monoclonal cell strain having a high Meg-CSF-productivity, from the cell strain PC-13 of human large cell lung cancer, and further in recovering the Meg-CSF substance from the supernatant of the culture of the cells of the MC-1 strain. In a still further aspect of the present invention, therefore, there is also provided a strain of human lung cancer cell, which has been isolated, as a monoclonal strain having a high ability to produce a megakaryocyte colony stimulating factor, from a cell strain of a human large cell lung cancer.

Figure 1:
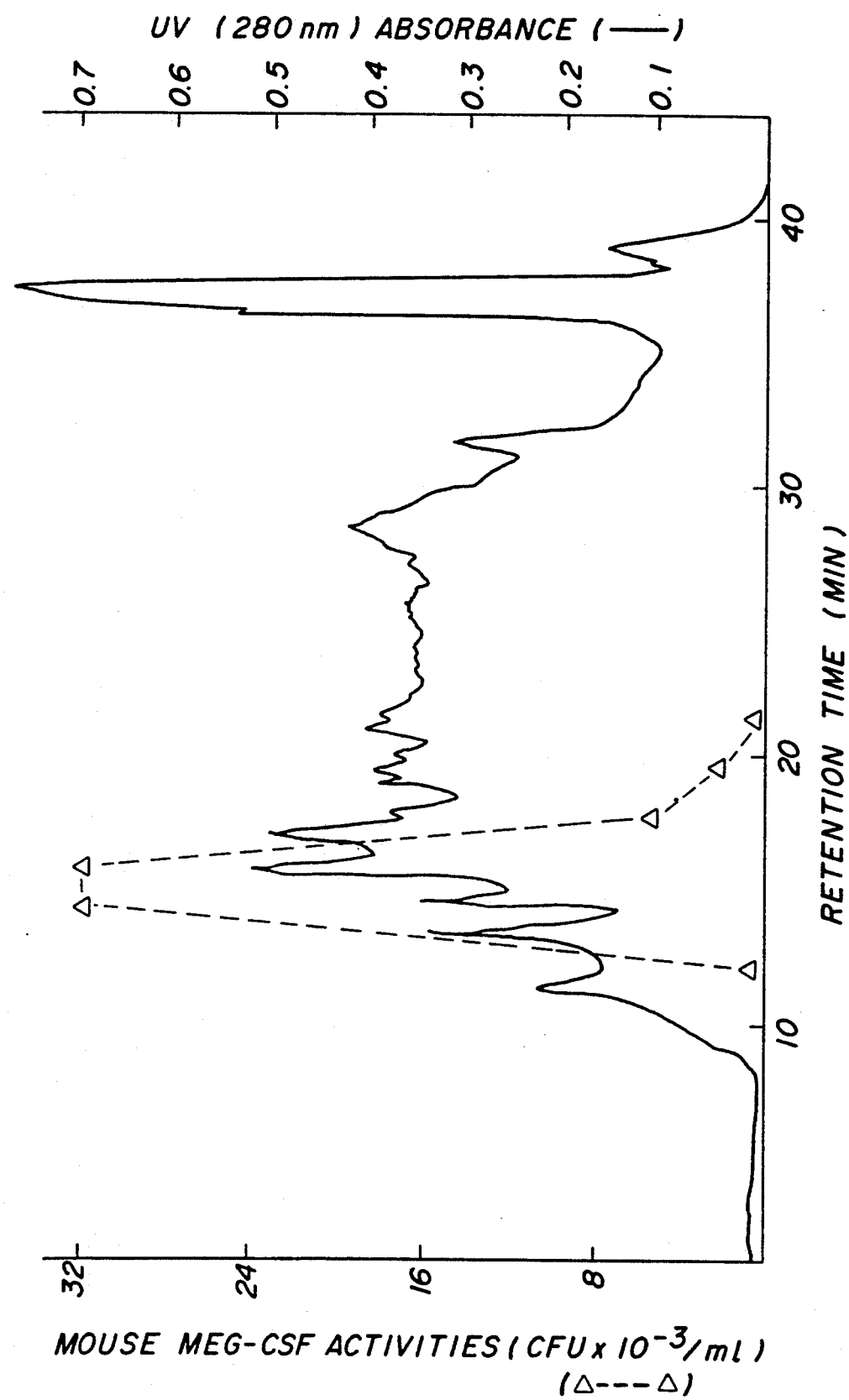
FIG. 1 shows a chromatogram for representing the pattern that the Meg-CSF activities of the eluate fractions and the absorbance of the eluate fractions for ultraviolet rays (UV) at 280 nm wavelength changed as a function of the retention time of each eluate fraction, as the eluate fractions were collected in the course of purification of the Meg-CSF substance, wherein the Meg-CSF substance which had been partially purified in the preceding steps was further purified by ion-exchange chromatography on the ion-exchanger "Mono Q" (product of Pharmacia Company) in the process of Example 4 which demonstrates an illustrative production of the Meg-CSF substance of the present invention.

The present invention will next be described with reference to Examples. It is however to be noted that the present invention is not limited to these Examples.

EXAMPLE 1

The activities of the megakaryocyte colony stimulating factor, which was present in the supernatant of the culture (the conditioned medium) as obtained by culturing a cell strain of a human large cell lung cancer in accordance with the present invention, were investigated by the following two methods:

(1) Human plasma clot method

An aqueous solution of calcium chloride (40 $\mu$l, 2.6 $\mu$g/ml) was added to 360 $\mu$l of Iscove's Modified Dulbecco's Medium (hereinafter abbreviated as "IMDM") which contained 20 $\mu$l of bovine plasma, 40 $\mu$l of human Group-AB plasma, 4 mg of bovine serum albumin, 10 $\mu$M of 2-mercaptoethanol, $2 \times 10^5$ human bone marrow mononuclear cells and 40 $\mu$l of a sample to be assayed. The resulting mixture was immediately placed at the center of a 35-mm culture dish so that the mixture was allowed to coagulate. IMDM (0.6 m$\mu$) was placed around the clot as formed. The samples to be assayed were respectively the supernatant (namely, the conditioned medium) recovered from the culture of human large cell lung cancer cell strain PC-13, the RPMI-1640 medium employed for the culturing of the cell strain PC-13 (as a blank control), and as a positive control, the supernatant of the culture of phytohemagglutinin-stimulated human peripheral lymphocytes (PHA-LCM) which are known to have the human Meg-CSF activities. The clots containing the mononuclear cells were incubated at 37° C. for 12 days in the presence of air containing 5% of $CO_2$. While identifying the megakaryocyte colonies as formed in the resultant incubated mixtures, the human Meg-CSF activities were assayed with aid of the anti-human factor VIII antibody (product of DAKO CO.).

As a result, the supernatant of the culture as obtained by culturing the cells of the PC-13 strain was found to exhibit the human Meg-CSF activities similarly to said PHA-LCM.

TABLE 1

| Sample | Human Meg-CSF activities (CFU/ml) |
|---|---|
| RPMI-1640 medium | 0.5 |
| Supernatant from the culture of cells of PC-13 strain | 43 |
| PHA-LCM | 125 |

(2) Murine fibrin clot method

After a mixture of 80 μl of fetal calf serum 0.2 mg of bovine fibrinogen (product of Sigma Chemical Co.), 0.2 units of bovine thrombin (product of Sigma Chemical Co.), $2 \times 10^5$ murine bone marrow of $BDF_1$ mouse (male), and 400 μl of IMDM containing 40μl of a sample to be assayed was mixed together, the resultant mixture was promptly placed at the center of a 35-mm culture dish so that the mixture was allowed to coagulate. Iscove's Modified Dulbecco's Medium (IMDM, 0.6 ml) was placed around the clot as formed. Samples to be assayed were respectively the supernatant of the culture as obtained by culturing human large cell lung cancer cell strain PC-13, the RPMI-1640 medium employed for the culturing of the cells of the PC-13 strain (as a blank control), and, as a positive control, the supernatant of the culture of murine myelomonocytic leukemia cell (WEHI-CM) which is known to have the murine Meg-CSF activities. The clots cotnaining the murine leukemia cells were incubated at 37° C. for 6 days in the presence of air containing 5% of $CO_2$. The murine Meg-CSF activities were assayed with identifying the formed megakaryocyte colonies by the acetylcholinesterase staining.

As a result, the supernatant of the culture as obtained by culturing the cells of the PC-13 strain was found to exhibit murine Meg-CSF activities similarly to said WEHI-CM.

TABLE 2

| Sample | Murine Meg-CSF activities (CFU/ml) |
|---|---|
| RPMI-1640 medium | 1 ± 1 |
| Supernatant from the culture of cells of PC-13 strain | 36 ± 4 |
| WEHI-CM | 49 ± 9 |

EXAMPLE 2

After the cells of the PC-13 strain in the logarithmic growth phase were suspended at an adjusted concentration of 2 cells/ml in an RPMI-1640 medium containing 10% of fetal calf serum, the resultant cell suspension was placed in the wells of a 96-well microplate at a rate of 0.1 ml/well, followed by incubation at 37° C. in the presence of 5% $CO_2$.

Fifty-seven monoclonal cell strains, which had been obtained by the incubation of the cells in the individual wells, were separately removed and then allowed to proliferate. The proliferated cells of the 57 separate strains were individually inoculated at the inoculum size of $1 \times 10^5$ cells/ml in 20-ml aliquots of an RPMI-1640 medium containing 5% of fetal calf serum, followed by incubation at 37° C. for 4 days in the presence of 5% $CO_2$.

The resulting conditioned media (supernatants of the cultures) were separately dialyzed against Dulbecco's PBS of a 1/20-fold concentration and then lyophilized. Crude powder samples containing the Meg-CSF substance were individually dissolved in 1 ml aliquots of distilled water. The murine Meg-CSF potency of each of the resulting solutions was evaluated by the murine fibrin clot method. As a result, a particular, monoclonal cell strain having a higher ability to produce the megakaryocyte colony stimulating factor than the PC-13 strain which showed an Meg-CSF potency of 270 CFU/ml, was obtained, and said particular monoclonal cell strain has exhibited an Meg-CSF potency of 470 CFU/ml. This particular monoclonal cell strain was designated as "human lung cancer cell strain MC-1".

This human lung cancer cell strain MC-1 has been deposited under the deposit number of "FERM BP-2574" in a depository "Fermentation Research Institute", Agency of Industrial Science and Technology, Ministry of International Trade and Industry, Government of Japan.

EXAMPLE 3

Cells of the human lung cancer cell strain MC-1, which belongs to the cells of a human large cell lung cancer, were cultured at an initial concentration of $1 \times 10^5$ cells/ml and at 37° C. for 4 days in the presence of 5% $CO_2$ in such a serum-free medium having the composition indicated below in Table 4 (namely, the RPMI-HPTS medium as described above). Thereafter, 100 ml of the culture supernatant (conditioned medium) were recovered from the resulting culture. The conditioned medium thus obtained was dialyzed against Dulbecco's PBS of a 1/20-fold concentration, followed by lyophilization of the dialyzate. The resulting powder contained the Meg-CSF substance and was dissolved in 5 ml of distilled water. The murine Meg-CSF activities of the resultant aqueous solution were evaluated by the murine fibrin clot method. As a control was employed such powder that obtained by processing the RPMI-HPTS medium in the same manner as described above, except that the inoculation with cells of the MC-1 strain was omitted.

As a result, the cells of the MC-1 strain have been found to produce the Meg-CSF substance even when they are cultured in a serum-free medium.

TABLE 3

| Sample | Murine Meg-CSF activities (CFU/ml) |
|---|---|
| Supernatant from the culture of the MC-1 strain | 640 ± 70 |
| RPMI-HPTS medium | 17 ± 10 |

TABLE 4

| Composition of the RPMI-HPTS medium (per 10 l) | |
|---|---|
| RPMI-1640 medium, as a powder form (product of Nissui Pharmaceutical Co., Ltd.) | 104 g |
| Sodium hydrogen carbonate (product of Nacalai Tesque, Inc.) | 12 g |
| Penicillin G (product of Meiji Seika Kaisha, Ltd.) | 400 mg |
| Streptomycin (product of Meiji Seika Kaisha, Ltd.) | 400 mg |
| Transferrin (product of Boehringer Mannheim GmbH) | 50 mg |
| Selenious acid (product of Nacalai Tesque, Inc.) | 200 μg |
| Sodium pyruvate (product of Sigma Chemical Co., Ltd.) | 1.0 mM |
| HEPES (product of Nacalai Tesque, Inc.) | 15.0 mM |

EXAMPLE 4

This example illustrates a method which is suitable for culturing the human lung cancer cell strain MC-1, namely a cell strain having a high Meg-CSF-productivity, and recovering the Meg-CSF substance from the resultant supernatants of the cultures, followed by purifying the Meg-CSF substance.

1. Culturing

The MC-1 strain (FERM BP-2574) as obtained in Example 2 was allowed to proliferate at 37° C. under humidity-saturated air in the presence of 5% of $CO_2$ in an RPMI-1640 medium containing 5% of fetal calf serum (product of Nissui Pharmaceutical Co., Ltd.) in Petri dishes until $1 \times 10^9$ cells were obtained. Those cells of the MC-1 strain were washed with Dulbecco's PBS, followed by treatment with a trypsin-EDTA solution (Product of GIBCO Laboratories). Two to five minutes later, the enzyme reaction was terminated by a trypsin inhibitor (product of Sigma Chemical Co., Ltd.). Cells which had been removed and collected from the wall of the culture vessel by pipetting were washed with Dulbecco's PBS and then suspended in a serum-free medium to be used. After the number of the cells was counted, they were used as inoculating cells.

The serum-free medium employed here for the production of Meg-CSF was the above-described RPMI-HPTS medium which contained RPMI-1640 medium as a basal medium.

As the culture vessel were used a tissue-culturing, rectangular Petri dishes ($25 \times 25$ cm in sizes, a product of Nunc Company) whose inner wall had been treated with collagen ("CELL MATRIX-1P"; product of Iwaki Glass Co., Ltd.). The MC-1 strain cells were inoculated at a rate of $1 \times 10^7$ cells per Petri dish to 100 Petri dishes in each of which 125 ml of the RMPI-HPTS medium had been placed and incubated beforehand at 37° C. under humidity-saturated air in the presence of 5% $CO_2$. The cells in those Petri dishes were cultured at 37° C. under humidity-saturated air in the presence of 5% $CO_2$. In the course of the culturing, the culture medium was replaced by aliquots of the fresh medium eight times at intervals of 3-4 days, whereby totally 100 liters of the supernatants of the culture, namely the conditioned medium were recovered.

2. Recovery of the active substance from the culture supernatant.

The resultant supernatant was filtered. The filtrate was forced to pass at a rate of 25 liters per column at the flow rate of 80 ml/min through columns of hydroxyapatite (90 mm in diameter $\times 60$ mm in length; products of Seikagaku Kogyo Co., Ltd.) which had been equilibrated with a 10 mM potassium phosphate buffer (pH 6.8), so that the active substance was adsorbed on the hydroxyapatite. After each column was washed with 2,000 ml of a 10 mM potassium phosphate buffer (pH 6.8) at a flow rate of 80 ml/min, the active substance was eluted with a 0.5M potassium phosphate buffer (pH 6.8) at a flow rate of 10 ml/min.

The eluate was collected in 10-ml fractions. Those eluate fractions were monitored by measuring their absorbance of ultraviolet rays (at 280 nm). The fractions which showed the UV absorption were recovered as active fractions. The total amount of the protein in the active fractions was 2,280 mg.

3. Chromatography on Con A-agarose column

The active fractions (1.8 l) as recovered in the preceding step were dialyzed against a 10 mM sodium chloride-10 mM sodium phosphate buffer (pH 7.2), so that 2.0 liters of the dialyzate were obtained. This dialyzate solution was divided into equal halves (1.0 liter) and then caused to pass at the flow rate of 3.5 ml/min through a column of Con A-agarose (42 mm in diameter $\times 77$ mm in length; products of Seikagaku Kogyo Co., Ltd.) which had been equilibrated with a 10 mM sodium chloride-10 mM potassium phosphate buffer (pH 7.2). The effluents from the column were combined together. The total amount of the protein in the effluents was 1,590 mg.

4. Ion-exchange chromatography

The Con A-agarose column effluents were divided into 225-ml portions, followed by dialysis against a 10 mM sodium phosphate buffer (pH 7.0). The resulting dialyzate was caused to flow at the flow rate of 4 ml/min through a column of an ion-exchanger "Mono Q HR10/10" (10 mm in diameter $\times 100$ mm in length; product of Pharmacia Company) which had been equilibrated with the same buffer, whereby the active substance was adsorbed on the "Mono Q" substance. After the column was washed with the same buffer, the active substance was eluted with a 10 mM sodium phosphate buffer (pH 7.0) plus 0-500 mM sodium chloride by the gradient elution manner, at a flow rate of 4 ml/min. The eluate was collected in 10-ml fractions. The ultraviolet ray (at 280 nm) absorbance and murine Meg-CSF activities of each fraction were measured. FIG. 1 of the accompanying drawings shows changes in the UV absorbance and Meg-CSF activities as a function of the retention time of each fraction. The changes in the UV absorbance are indicated by the broken curve, while the changes in the activities are shown by the solid curve. This equally applies to FIG. 2 and FIG. 3. The active fractions which were eluted at the salt concentration of about 150 mM were collected together. The total amount of the protein in this active fraction was 78 mg.

5. Gel filtration

Figure 2:
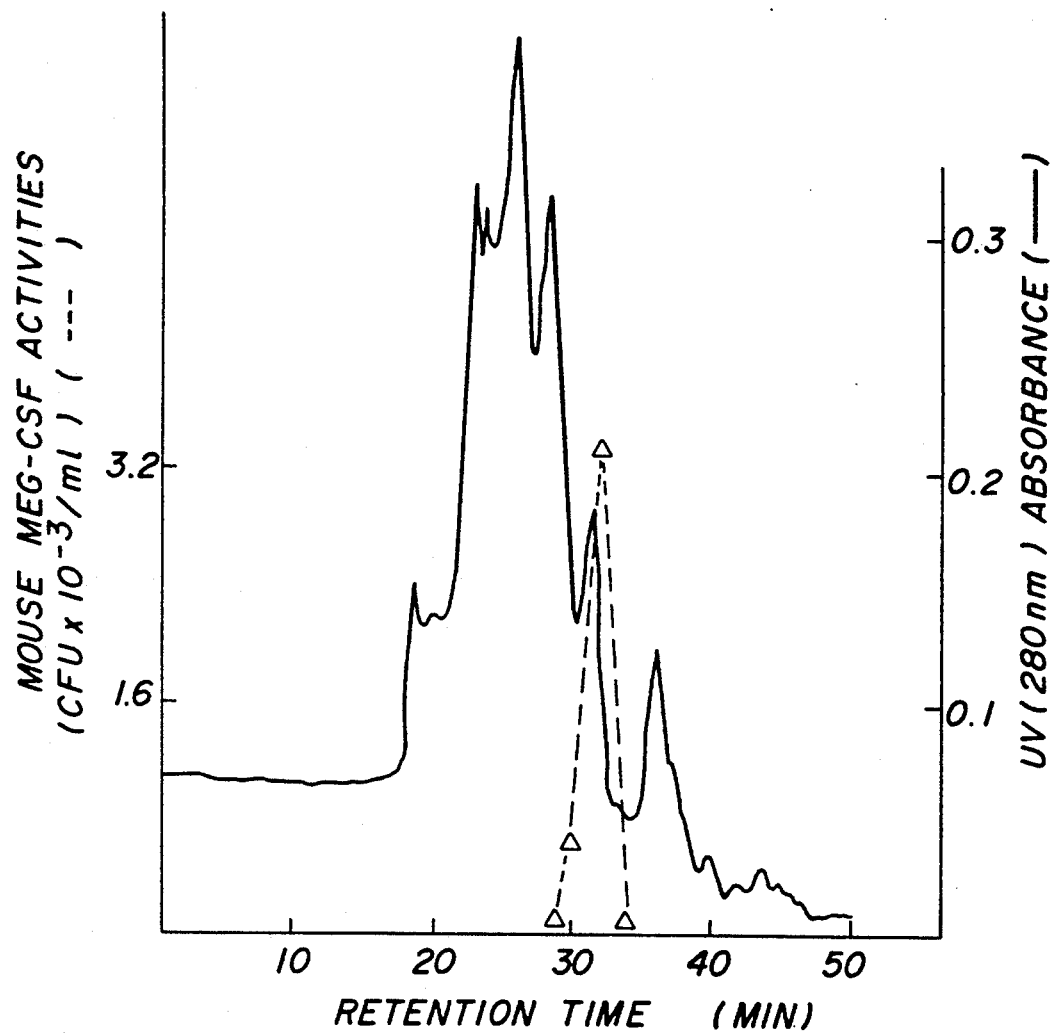
FIG. 2 shows a chromatogram for depicting the pattern that the Meg-CSF activities of the eluate fractions and the absorbance of the eluate fractions for ultraviolet rays (UV) at 280 nm wavelength changed as function of the retention time of each eluate fraction, as the eluate fractions were collected in the course of purification of the Meg-CSF substance, wherein the Meg-CSF substance which had been partially purified in the ion-exchange chromatographic purification step of Example 4 was further purified in a gel-filtration step with making use of "TSK gel G2000 SW" (product of TOSOH CORP.) as a gel-filtration carrier.
Figure 3:
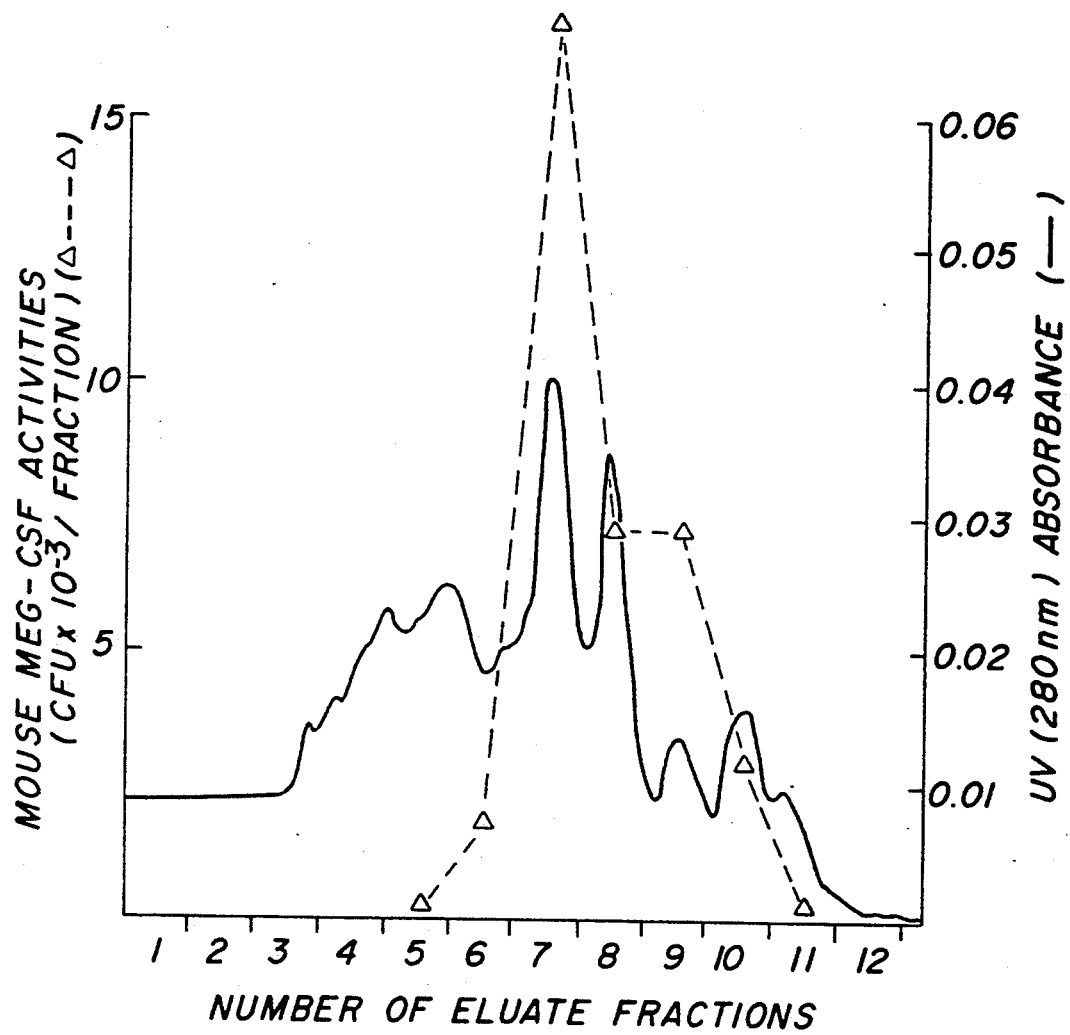
FIG. 3 shows a chromatogram for depicting the pattern that the Meg-CSF activities of the eluate fractions and the absorbance of the eluate fractions for ultraviolet rays (UV) at 280 nm wavelength changed as function of the order of eluting of the eluate fractions in the course of further purification of the Meg-CSF substance, wherein the Meg-CSF substance which had been purified in the purification step with gel-filtration in Example 4, was further purified in a hydroxyapatite column (product of Kanto Chemical Co., Inc.) using hydroxyapatite as an adsorbent.

The active fraction (100 ml) as recovered from the "Mono Q" column was dialyzed against a 5 mM sodium sulfate-5 mM sodium phosphate buffer (pH 7.2), followed by lyophilization of the resulting dialyzate. The resulting, partially-purified powder containing the Meg-CSF substance was added to and dissolved in 5 ml of distilled water. After insoluble matter was removed by centrifugation from the resulting solution, the solution was added in 1-ml portions to a TSK gel G2000 SW column (21.5 mm in diameter $\times 600$ mm in length; product of TOSOH CORP.) plus a TSK guard column SW (21.5 mm in diameter $\times 75$ mm in length; product of TOSOH CORP.), which had been equilibrated with a 100 mM sodium sulfate-100 mM sodium phosphate buffer (pH 7.2). The active substance was then developed with the same buffer at the flow rate of 5 ml/min. The effluent from the column was collected in 5 ml-fractions, and the ultraviolet ray (280 mn) absorbance and murine Meg-CSF activities of each fraction were measured. FIG. 2 of the accompanying drawings shows changes in the UV absorbance and the Meg-CSF activities as a function of the retention time of each fraction. The active fractions eluted at the retention time of about 30-32 minutes were recovered. The total amount of the protein in the resulting active fractions was 5.1 mg.

6. Chromatography on hydroxyapatite column

After 50 ml of the active fraction as recovered from the gel filtration column were diluted with 50 ml of distilled water, the diluted solution was caused to pass at the flow rate of 1 ml/min through a column of hydroxyapatite (8 mm in diameter ×100 mm in length; product of Kanto Chemical Co., Inc.) which had been equilibrated with a 50 mM sodium phosphate buffer (pH 7.2), so that the active substance was adsorbed on the hydroxyapatite (HA). The column was then eluted with 50 mM-300 mM sodium phosphate buffers (pH 7.2) in the gradient elution manner, at a flow rate of 1 ml/min. The eluate was collected in 5 ml-fractions. The ultraviolet ray (280 nm) absorbance and murine Meg-CSF activities of each fraction were measured. The results of measurement are shown by curves in FIG. 3 of the accompanying drawings. Active fractions (Fraction Nos. 6–10) which were eluted at the phosphate concentration of about 240 mM were collected. The content of the protein in those active fractions was 0.24 mg. The active fractions were dialyzed against a 150 mM sodium chloride-10 mM sodium phosphate buffer (pH 7.2) so that the Meg-CSF substance as a final product was obtained in the form of a water-soluble substance.

TABLE 5

| Active fractions obtained in individual steps for recovery and purification | Meg-CSF activities (CFU/ml) | Protein (mg) |
| --- | --- | --- |
| Active fraction recovered from the culture supernatant through hydroxyapatite column | 4.4 × 10$^6$ | 2,280 |
| Con A-agarose | 7.4 × 10$^6$ | 1,590 |
| "Mono Q" chromatography | 4.8 × 10$^6$ | 78 |
| Gel filtration | 2.5 × 10$^5$ | 5.1 |
| Hydroxyapatite (HA) chromatography | 1.6 × 10$^5$ | 0.24 |

EXAMPLE 5

Properties of the megakaryocyte colony stimulating factor substance of the present invention, which was obtained as the final product in the fifth step for the recovery made in Example 4, were investigated as follows:

1. Molecular weight

The molecular weight of the above Meg-CSF substance (hereinafter called "the present substance") was measured by a gel-filtration method in which highperformance liquid chromatography was made under the under-mentioned conditions. The molecular weight of the present substance was found to amount to about 24,000.

Column: "TSK gel G2000 SW" (21.5 mm in diameter ×600 mm in length; product of TOSOH CORP.)
Solvent: 100 mM sodium phosphate (pH 7.2)+100 mM Na$_2$SO$_4$
Flow rate: 5.0 ml/min The calculation of the molecular weight of the present substance was conducted through its comparisons with bovine serum albumin (molecular weight: 67,000), ovalbumin (molecular weight: 43,000), carbonic anhydrase (molecular weight: 29,000) and ribonuclease A (molecular weight: 13,700) as standard proteins having known values of the molecular weight.

2. Isoelectric point

Using isoelectric chromatography, the isoelectric point of the present substance was measured under the following conditions. The present susbtance was found to have an isoelectric point of pI=4.5–5.5.
Column: "Mono P" (product of Pharmacia Company)
Initiation solvent: 25 mM bis-Tris-iminodiacetate buffer (pH 7.1)
Developer solvent: 10% polybuffer 74-iminodiacetate buffer (pH 4.0)
Flow rate: 0.5 ml/min 3. Thermal stability Samples of the present substance were held at 25° C., 56° C. and 80° C., respectively for 30 minutes in Dulbecco's PBS (product of Nissui Pharmaceutical Co., Ltd.), and the residual murine Meg-CSF activities were measured. As a result, this substance was unstable at 80° C.

TABLE 6

| Temperature | 25° C. | 56° C. | 80° C. |
| --- | --- | --- | --- |
| Residual activities (%) | 100 | 88 | 2 |

4. Stability to enzyme

The present susbtance was treated at 37° C. for 5 hours with 0.5 unit of insoluble neuraminidase (product of Sigma Chemical Co., Ltd.) in a 0.1 M aqueous sodium acetate solution (pH 5.0). The residual murine Meg-CSF activities were evaluated. This substance was stable to said enzyme.

TABLE 7

| Enzyme | Residual activities (%) |
| --- | --- |
| Non addition | 100 |
| Neuraminidase | 100 |

5. Activities of cytokines

Investigation was made as to whether the present substance has the respective activities of known cytokines, namely, IL-2, IL-6, TNF and EPO. The methods of measuring these respective activities were as follows:

[IL-2]

Murine IL-2 dependent cells, namely the cell strain CTLL-2, were cultured. The resulting cells were incubated overnight in the presence of the present substance or IL-2 as a standard sample, followed by pulse-labeling with [$^3$H] thymidine. The potency of IL-2 was calculated through its comparison with that obtained using the standard sample.

[IL-6]

SKW6-C1 strain originated from the B-cells were cultured. The resulting cells were incubated for 4 days in the presence of the present substance or IL-6 as a standard sample. Induction of IgM production was measured by ELISA. The potency of IL-6 was calculated through its comparison with that obtained using the standard sample.

[TNF]

Murine fibroblasts, L929 strain, was incubated by the monolayer culture method. The resulting cells were further incubated overnight in the presence of the present substance or TNF as a standard sample, followed by pulse-labeling with [$^3$H] thymidine. The cytotoxicity occurred on the L929 strain cells was determined through its comparison with that obtained using the standard sample.

[EPO]

Murine fetal liver cells were incubated for 20 hours in the presence of the present substance or EPO as a standard sample. The medium was then replaced, followed by pulse-labeling with [$^{54}$Fe] iron citrate. The potency of EPO was determined based through its comparison with that obtained using the standard sample.

TABLE 8

| Activities | Potency value as measured |
|---|---|
| IL-2 | Less than the detectable limit |
| IL-6 | " |
| TNF | " |
| EPO | " |

6. Antigenecity

Investigation was made as to whether the present substance has immunological reactivity with cytokine and hormones.

Firstly, there was carried out an experiment wherein the present substance was reacted with an anti-human IL-1 antibody for neutralization purpose. Rabbit polyclonal antibodies (product of Genzyme Corp.) for human IL-1α and human IL-1β were used as antibodies, and the level of each neutralizing antibody in the neutralization reaction mixture was adjusted to 200 NU/ml. As a result, the Meg-CSF activities of the present substance were not reduced even when it was treated with anti-human IL-1α antibody or anti-human IL-1β antibody. It was hence found that the present substance does not immunologically react with the antibodies described above.

Similarly, experiments for neutralization of the present substance were conducted by reaction with anti-human GM-CSF antibody and anti-human IL-3 antibody. Rabbit polyclonal antibodies (product of Genzyme Corp.) for human GM-CSF and human IL-3 were used as antibodies. As a result, the activities of the present substance were not reduced even when it was treated with anti-human GM-CSF antibody or anti-human IL-3 antibody. It was therefore found that the present substance does not immunologically react with the antibodies described just above.

The present substance was further investigated by radio-immunoassay. This substance was not found to exhibit the activities of prolactin, thyroid-stimulating hormone (TSH), growth hormone (GH), insulin, vasopressin (ADH) or adrenocorticotropic hormone (ACTH). It was accordingly found that the present substance is immunologically distinct from these hormones.

7. Stability to solubilizers

Investigation was made as to whether the present substance remains stable when it was treated with protein solubilizers. Thus, the present substance was placed in Dulbecco's PBS and then incubated at 4° C. for 24 hours in the presence of various solubilizers. After the solubilizers were removed by dialysis from the resultant incubated solutions, the murine Meg-CSF activities still remaining in the solutions were assayed. As a result, the present substance was partially deactivated and was unstable when it was treated with a 2% aqueous SDS solution or with a 3M aqueous guanidine hydrochloride solution. But, the present substance remained stable even when it was treated with a non-ionic surface-active detergent, such as 0.02% Tween 20, 0.01% NP-40 and 0.01% Triton ×100 in solution in water. The results of these stability experiments are summarized in the following table.

TABLE 9

| Solubilizer | Residual activities (CFU/ml) |
|---|---|
| Control | 175 ± 10 |
| Guanidine hydrochloride | 50 ± 17 |
| SDS | 46 ± 13 |
| Tween 20 | 150 ± 17 |
| NP-40 | 158 ± 17 |
| Triton X 100 | 180 ± 12 |

EXAMPLE 6

To investigate whether or not the Meg-CSF activities of the Meg-CSF substance of the present invention are developed via T-cells or monocytic cells contained in the bone marrow cells, the Meg-CSF substance of the present invention was applied to bone marrow cells from which T-cells or phagocytes had been eliminated. The developed Meg-CSF activities were measured by the murine fibrin clot method.

1. Activities of Meg-CSF substance on bone marrow cells from which T-cells had been eliminated.

BDF$_1$ mouse femoral bone marrow cells were suspended at the concentration of 1×10$^7$ cells/ml in a cyto-toxicity-testing medium (product of Cedarlane Laboratories Ltd.), followed by addition of a solution of an anti-Thy-1,2 monoclonal antibody (product of Cedarlane Laboratories). The resultant mixture was allowed to stand at 4° C. for 60 minutes. After the supernatant was removed by centrifugation from the mixture, a solution of a lowtoxicity rabbit complement (Product of Cedarlane Laboratories Ltd.) was added to the cells so separated. Subsequent to incubation of the resulting cell suspension at 37° C. for 60 minutes, the cell suspension was layered over 4 ml of Lympholyte-M (product of Cedarlane Laboratories Ltd.) and centrifuged at 500× g for 20 minutes. Mononuclear cell fraction was collected. The mononuclear cells were washed twice with IMDM (product of Sigma Chemical Co., Ltd.) and then suspended in IMDM at the cell concentration of 7.5×10$^6$. Various volumes of an aqueous solution of the final product of the Meg-CSF substance of this invention, which had been obtained in Example 4, as the sample to be assayed, were added to portions of the cell suspension prepared as above, followed by incubation. The murine Meg-CSF activities of the Meg-CSF substance of the present invention were evaluated by the above-described murine fibrin clot method. The results obtained are summarized below. The Meg-CSF substance of the present invention exhibited dose-dependent Meg-CSF activities even when it was applied to the bone marrow cells from which T-cells had been eliminated.

TABLE 10

| Amount of sample (μl) | Meg-CSF activities (CFU) |
|---|---|
| 1 | 2.7 ± 1.5 |
| 5 | 16.7 ± 2.1 |
| 10 | 30.3 ± 1.5 |
| 20 | 38.0 ± 1.4 |

2. Activities of Meg-CSF substance for bone marrow cells from which phagocytes had been eliminated.

BDF$_1$ mouse femoral bone marrow cells were added to IMDM (product of Sigma Chemical Co., Ltd.,) which contained 20% of fetal calf serum (product of GIBCO Laboratories). The cell concentration was adjusted to 5×10$^6$ cells/ml. The resultant cell suspension was added with a 1/9th volume of a carbonyl iron solution (40 mg/ml; product of Nacalai TESQUE, INC.) or with IMDM (product of Sigma Chemical Co., Ltd.), followed by incubation at 37° C. for 45 minutes. The thus-incubated cell suspensions were individually layered over 4 ml of Lympholyte-M (product of Cedarlane Laboratories), followed by centrifugation at 500× g for 20 minutes. Mononuclear cell fraction was collected. The mononuclear cells were washed twice with IMDM (product of Sigma Chemical Co., Ltd.) and then suspended in IMDM at the cell concentration of $1 \times 10^7$. The Meg CSF substance of this invention was added to each of the cell suspensions so prepared. The Meg-CSF activities as developed were measured by the above-described murine fibrin clot method. The activities of the Meg-CSF substance of the present invention were evaluated in the above described manner.

The results obtained are summarized in the next table. Even when the bone marrow cells from which the phagocytes had been eliminated were used and reacted with the Meg-CSF substance of the present invention, the Meg-CSF substance of the present invention showed Meg-CSF activities similar to those exhibited in the case where the Meg-CSF substance of this invention was applied to the bone marrow cells from which the phagocytes had not been eliminated.

TABLE 11

| Bone marrow cells tested | Meg-CSF activities (CFU) |
| --- | --- |
| Phagocyte-eliminated bone marrow cell group | 30.0 ± 4.6 |
| Control group | 28.3 ± 4.2 |

EXAMPLE 7

"In vitro" effects of the Meg-CSF substance of this invention, which had been obtained as the final product in Example 4, on megakaryocyte cells were investigated.

1. Effects on murine megakaryocyte progenitor cells (1) PBS (phosphate buffered saline) containing the Meg-CSF substance of this invention at the concentration of 160 CFU/0.20 ml was intraperitoneally administered once to $BDF_1$ mice (male, 8-weeks old). Upon elapsed times of 0, 24, 48, 72 and 96 hours after the administration, the mice were sacrificed successively. The numbers of megakaryocyte progenitor cells in the excised femoral marrow and the excised spleen were counted immediately. The counting of megakaryocyte progenitor cells was conducted by suspending them in 2 ml of IMDM in the case of marrow cells of the bemer, and suspending in 4 ml of IMDM in the case of spleen cells. Each of the cell suspensions so prepared was incubated by the murine fibrin clot method, with adding the cell suspension and a medium conditioned by poke weed-mitogen-stimulated spleen cells (PWM-SCM), each in a proportion of 5%. The number of acetylcholinesterase-staining positive cells which were matured by PWM-SCM was counted. The numbers of megakaryocyte progenitor cells (CFU-Meg) which are contained in the spleen and the femoral marrow, respectively, are evaluated and are shown in the following table.

TABLE 12

| Time elapsed after administration | CFU/Meg spleen | CFU-Meg/ femoral marrow |
| --- | --- | --- |
| 0 hrs. | 4560 ± 1410 (100%) | 6440 ± 1067 (100%) |

TABLE 12-continued

| Time elapsed after administration | CFU/Meg spleen | CFU-Meg/ femoral marrow |
| --- | --- | --- |
| 24 hrs. | 5254 ± 1399 (115%) | 6909 ± 1020 (107%) |
| 48 hrs. | 8711 ± 1117 (191%) | 6400 ± 557 (99%) |
| 72 hrs. | 7523 ± 2006 (165%) | 6875 ± 311 (107%) |
| 96 hrs. | 6525 ± 881 (143%) | — |

(2) In a manner similar to that described above, mice were sacrificed upon an elapsed time of 48 hours after they were administered with the Meg-CSF substance of the present invention. The number of megakaryocyte progenitor cells (CFU-Meg) in the spleen as excised from each mouse was then counted, whereby the dose-dependency of the activity of this substance for the proliferation CFU-Meg was assayed. The results obtained are shown in the following table.

TABLE 13

| Dosage of Meg-CSF substance | CFU-Meg/spleen |
| --- | --- |
| Not treated | 4560 ± 1410 (100%) |
| 40 CFU | 5944 ± 1635 (130%) |
| 80 CFU | 7245 ± 2010 (159%) |
| 160 CFU | 8711 ± 1117 (191%) |

2. Effects on megakaryocyte in the mouse spleen

PBS containing the Meg-CSF substance of this invention at the concentration of 160 CFU/0.20 ml was intraperitoneally administered once to $BDF_1$ mice (male, 8-weeks old). Upon elapsed times of 0, 24, 48 and 72 hours after the administration, the mice were sacrificed successively. The number of megakaryocyte progenitor cells in the spleen as excised from each mouse was counted immediately. Upon counting of the cells, the spleen was fixated with aqueous 10% formaldehyde and embedded in paraffin. A sectioned specimen was then prepared from the spleen to give a largest cross-sectional area. After the sectioned specimen was subjected to the HE staining (hematoxylineosin staining), the number of megakaryocytes so stained was counted under a microscope and the number of megakaryocytes per unit area of red pulp was then calculated. The results obtained are summarized in the following table.

TABLE 14

| Time elapsed after administration | Number of megakaryocytes per $mm^3$ of red pulp | Level of significance |
| --- | --- | --- |
| 0 hrs. | 13 ± 1.8 (100%) | |
| 24 hrs. | 15 ± 1.8 (115%) | p < 0.03 |
| 48 hrs. | 20 ± 3.5 (150%) | p < 0.01 |
| 72 hrs. | 18 ± 1.3 (140%) | p < 0.005 |

3. Effects on platelets in mouse peripheral blood

PBS containing the Meg-CSF substance of this invention at the concentration of 160 CFU/0.20 ml was intraperitoneally administered once to $BDF_1$ mice (male, 8-weeks old, 6 mice/group). Upon elapsed times of 0, 48 and 96 hours after the administration, it was observed that the number of platelets in the peripheral blood increased with significance. The test results are shown in the following table.

TABLE 15

| Time elapsed after administration | Number of platelets ($\times 10^4/\mu l$) |
| --- | --- |
| 0 hrs. | 116 ± 14 (100%) |
| 48 hrs. | 123 ± 10 (106%) |

TABLE 15-continued

| Time elapsed after administration | Number of platelets ($\times 10^4/\mu l$) |
| --- | --- |
| 96 hrs. | 140 ± 13 (121%) |

INDUSTRIAL APPLICABILITY

As has been described above, the present invention has made it possible to culture a cell strain of a human large cell lung cancer and then to isolate, from the supernatant or the resulting conditioned medium of the culture of the cell, a megakaryocyte colony stimulating factor (Meg-CSF) substance having the above-described physiological activities. This invention can therefore provide, as a medicine, the Meg-CSF substance which is useful for therapeutic treatment of certain thrombocytopenia.

We claim:

1. A megakaryocyte colony stimulating factor which comprises a protein as isolated from the supernatant of the culture obtained by cultivation of a cell strain of a human large cell lung cancer and which exhibits the activity of forming a megakaryocyte colony when said factor is applied to human or murine bone marrow cells in vitro, and also exhibits the activity of increasing the number of platelets in peripheral blood in vivo upon intraperitoneal administration of said factor in mice, significantly over the number of platelets observed in peripheral blood of the mice receiving no intraperitoneal administration of said factor and further has the following properties:

(a) Said factor can be isolated from the supernatant of the culture of human large cell lung cancer cell strain PC-13 or from the supernatant of the culture of human lung cancer cell strain MC-1 and having been isolated as a monoclonal strain from the PC-13 strain;

(b) Molecular weight: 24,000 Daltons, as measured by gel filtration;

(c) Isoelectric point: 4.5–5.5, as measured by isoelctric chromatography;

(d) Thermal stability of activities: the factor can be deactivated when the factor is heated at 80° C. for 30 minutes, and hence the activities of the factor do not have thermal stability;

(e) Stability of activities against enzyme: The activities of the factor remain stable even when the factor is treated with neuraminidase;

(f) Absence of cytokine activity: The factor does not show the activity of cytokine selected from the group consisting of interleukin-2, interleukin-6, tumor necrosis factor and erthropoietin;

(g) Antigenecity: The activities of the factor are not neutralized by antibody selected from the group consisting of anti-interleukin-1α antibody, anti-interleukin-1β antibody; anti-human GM-CSF antibody and anti-human interleukin-3 antibody; when evaluated by radioimmunoassay, the factor does not exhibit immunological cross reaction with any one of a hormone selected from the group consisting of prolactin, thyroid-stimulating hormone (TSH), growth hormone (GH), insulin, vasopressin (ADH) and adrenocorticotropic hormone (ACTH);

(h) Stability of activities against solubilizers: When the factor is treated with sodium dodecylsulfate (SDS) or guanidine hydrochloride, the activities of the factor are partially lost but the activities of the factor remain substantially stable even when the factor is treated with a non-ionic surface-active detergent;

(i) Characteristic physiological activities: The factor shows the activity of forming a megakaryocyte colony when the factor is applied to human or murine bone marrow cells in vitro; the factor also exhibits the activity of promoting proliferation of megakaryocytes and megakaryocyte progenitor cells in the spleen and the activity of increasing the number of platelets in peripheral blood when the factor is administered to a mouse.

2. A process for the preparation of a megakaryocyte colony stimulating factor which comprises cultivating a cell strain of a human large cell lung cancer strain MC-1 having all the identifying characteristics of FERM BP-2574; separating from the resulting culture of said cell strain the supernatant containing therein the megakaryocyte colony stimulating factor, recovering said factor from the supernatant, and then purifying said factor.

3. The process of claim 2, wherein the cell strain of the human large cell lung cancer is cultivated in a culture medium containing no serum, namely, in a serum-free medium.

4. A process for the preparation of a megakaryocyte colony stimulating factor, which comprises cultivating human lung cancer cell strain MC-1 having all the identifying characteristics of FERM BP-2574 in a serum-free medium containing per 10 l of the medium 104 g (as measured in a powder form) of RPMI-1640 medium, 12 g of sodium hydrogen carbonate, 400 mg of penicillin G, 400 mg of streptomycin, 50 mg of transferrin, 200 μg of se'..i.ous acid, 1.0 mM of sodium pyruvate, 15.0 mM of HEPES and the balance being sterilized water (that is, in .'P/I-HPS medium) at a temperature of 35°–38° C., under air which contains 5% of $CO_2$ and has been saturated with humidity; and continuing the cultivation of the cells until the megakaryocyte colony stimulating factor is produced and acumulated in the supernatant of the resulting culture of said cancer cell strain.

* * * * *